United States Patent
Lee et al.

(10) Patent No.: US 10,289,807 B2
(45) Date of Patent: May 14, 2019

(54) SIMILARITY EVALUATION METHOD FOR STRUCTURAL EFFECT DETERMINING SOLVENT REACTIVITY, AND SYSTEM USING SAME

(71) Applicant: LG Chem, Ltd., Seoul (KR)

(72) Inventors: Seung-Yup Lee, Daejeon (KR); Ji-Won Jeong, Daejeon (KR); Mi-Ri Kim, Daejeon (KR); Kyoung-Shil Oh, Daejeon (KR); Kyoung-Hoon Kim, Daejeon (KR)

(73) Assignee: LG Chem, Ltd. (KR)

( * ) Notice: Subject to any disclaimer, the term of this patent is extended or adjusted under 35 U.S.C. 154(b) by 105 days.

(21) Appl. No.: 15/518,915

(22) PCT Filed: Jul. 19, 2016

(86) PCT No.: PCT/KR2016/007865
§ 371 (c)(1),
(2) Date: Apr. 13, 2017

(87) PCT Pub. No.: WO2017/014539
PCT Pub. Date: Jan. 26, 2017

(65) Prior Publication Data
US 2017/0242982 A1   Aug. 24, 2017

(30) Foreign Application Priority Data
Jul. 20, 2015 (KR) .................. 10-2015-0102614

(51) Int. Cl.
*G06F 11/30* (2006.01)
*G06F 19/00* (2018.01)
*G06F 17/18* (2006.01)

(52) U.S. Cl.
CPC ............ *G06F 19/703* (2013.01); *G06F 17/18* (2013.01); *G06F 19/704* (2013.01); *G06F 19/702* (2013.01)

(58) Field of Classification Search
CPC ................................................... G06F 19/703
See application file for complete search history.

(56) References Cited

U.S. PATENT DOCUMENTS 6,182,016 B1 * 1/2001 Liang .................. G06F 19/16
702/21
7,991,730 B2 * 8/2011 Wagner ............... G06F 19/702
702/27

FOREIGN PATENT DOCUMENTS

JP      2010182077 A    8/2010
KR      101346646 B1    1/2014

OTHER PUBLICATIONS

International Search Report from PCT/KR2016/007865, dated Nov. 9, 2016.
Bentley, et al., "Correclations and predictions of solvent effects on reactivity: some limitations of multi-parameter equations and comparisons with similarity models based on one solvent parameter." Journal of Physical Organic Chemistry, 2006, vol. 19, pp. 341-349.
Bhuvaneshwari and Elango, "Solvent Hydrogen Bonding and Structural Effects on Nucleophilic Substitution Reactions: Part 3. Reaction of Benzenesulfonyl Chloride with Anilines in Benzene/Propan-2-ol Mixtures", International Journal of Chemical Kinetics, vol. 39, No. 12, Dec. 2007, pp. 657-663.
Folic, et al., "Design of Solvents for Optimal Reaction Rate Constants", AIChE Journal, vol. 53, No. 5, May 2007, pp. 1240-1256.
Linert, et al., "Solvent Effects on Chemical Reactivity", Handbook of Solvents, 2nd Edition, vol. 1, ChemTec Publishing, Apr. 2014, pp. 753-810.
Supplementary European Search Report and Written Opinion for EP Application No. 16828043.6, dated Sep. 7, 2018.

* cited by examiner

*Primary Examiner* — Phuong Huynh
(74) *Attorney, Agent, or Firm* — Lerner, David, Littenberg, Krumholz & Mentlik, LLP

(57) ABSTRACT

This invention relates to a method of evaluating the similarity of structural effects of solvents determining solvent reactivity and a system using the same, and more particularly to a novel evaluation method that is able to quantitatively measure the structural effect of a solvent having an influence on reactivity upon reaction of the solvent with a predetermined material and to a system using the same.

10 Claims, No Drawings

SIMILARITY EVALUATION METHOD FOR STRUCTURAL EFFECT DETERMINING SOLVENT REACTIVITY, AND SYSTEM USING SAME

CROSS-REFERENCE TO RELATED APPLICATIONS

The present application is a national phase entry under 35 U.S.C. § 371 of International Application No. PCT/KR2016/007865, filed Jul. 19, 2016, which claims priority to and the benefit of Korean Patent Application No. 10-2015-0102614, filed Jul. 20, 2015, the disclosures of which are hereby incorporated by reference in their entirety into this application.

TECHNICAL FIELD

The present invention relates to a method of evaluating the similarity of structural effects of solvents that determine solvent reactivity and a system using the same. More particularly, the present invention relates to a novel evaluation method that is able to quantitatively measure the structural effect of a solvent having an influence on reactivity upon reaction of the solvent with a predetermined material and to a system using the same.

BACKGROUND ART

A solvent is able to be used in the preparation of a solution by dissolving a solute and is used as a reactant to synthesize a new material through the reaction with a predetermined material. Furthermore, a solvent is responsible for adjusting characteristics such as the surface properties of a target material by means of a material produced through the reaction to thus improve performance or impart novel functionality, and thus plays a great role in material development fields. When a solvent reacts with a predetermined material to give a novel product, the structural effect of the solvent has a great influence on the reaction rate or the reaction process. For example, even when the same solvent is used, a difference in reactivity may occur due to the structural effect thereof in a manner in which a reaction with a specific material progresses well but a reaction with another specific material does not progress. The reactivity difference of the solvent caused by the difference in the structural effect of the solvent is regarded as very important in determining the success of many chemical reactions. However, there is no method that enables the accurate evaluation or measurement of the structural effect of the solvent causing such a reactivity difference. Accordingly, in order to develop a new material having improved performance, it is necessary to develop a novel method of accurately evaluating the structural effect of the solvent that is capable of significantly affecting the reaction rate or reactivity.

DISCLOSURE

Technical Problem

Accordingly, the present invention has been made keeping in mind the problems encountered in the related art, and the present invention is intended to provide a novel method of quantitatively measuring the structural effect of a solvent that affects the reactivity upon reaction of the solvent with a predetermined material. Also, the present invention is intended to provide a novel method of quantitatively evaluating the individual structural effects of at least three solvents, whereby the structural effects of the solvents may be accurately measured, and also solvents that exhibit similar structural effects for specific solvents may be distinguished.

Technical Solution

Therefore, the present invention provides a method of evaluating the similarity of structural effects of solvents determining solvent reactivity, comprising the steps of:

a) selecting N solvents used for measuring the structural effects of solvents (wherein N is a natural number of 3 or more); and b) evaluating the structural effects of the N solvents selected in step a) through the following steps of i) to iv):

i) calculating $R(S_i)$ for the solvent $S_i$ among the N solvents selected in step a) using Equations 1 to 3 below;

$$R(S_i) = \frac{k_1 \times MV_1(S_i)^2 + k_2 \times MV_2(S_i) \times MV_{base}(S_i)}{MV_{base}(S_i) \times MV_1(S_i)} \quad \text{[Equation 1]}$$

$$MV_1(S_i) = m(S_i) \times N_A \quad \text{[Equation 2]}$$

$$MV_2(S_i) = w_1 \times \pi \times Rd^3 \quad \text{[Equation 3]}$$

(in Equations 1 to 3, $S_i$ is the $i^{th}$ solvent among the selected N solvents, $MV_{base}(S_i)$ represents the molar volume for the solvent $S_i$, $m(S_i)$ represents the molecular volume for the solvent $S_i$ and is a McGowan Molecular volume or a van der Waals volume, $N_A$ is the Avogadro constant, Rd represents a characteristic length for a molecular structure and is a Molecular Radius of Gyration, the constants $k_1$ and $k_2$ are real numbers excluding 0.0, and the constant $w_1$ is a real number greater than 0.0);

ii) setting a normal distribution using an average (AVG) and a standard deviation (SD) of N $R(S_i)$ values calculated in step i), thus calculating a cumulative distribution function for the N $R(S_i)$ values to determine a cumulative probability value $\rho(S_i)$;

iii) calculating $\Delta del(S_i,S_j)$, as a cumulative probability value difference for solvents $S_i$ and $S_j$, using Equation 4 below:

$$\Delta del(S_i,S_j) = |\rho(S_i) - \rho(S_j)| \quad \text{[Equation 4]}$$

(in Equation 4, $S_i$ is the $i^{th}$ solvent among the selected N solvents, and $S_j$ is the $j^{th}$ solvent among the selected N solvents); and iv) comparing $\Delta del(S_i,S_j)$ for the solvents $S_i$ and $S_j$ calculated in step iii) with the set cut-off value, whereby when $\Delta del(S_i,S_j)$ is equal to or less than the cut-off value $\delta_c$, structural effects of the solvents $S_i$ and $S_j$ are determined to be similar, and when $\Delta del(S_i,S_j)$ is greater than the cut-off value $\delta_c$, structural effects of the solvents $S_i$ and $S_j$ are determined to be different, thus quantitatively evaluating the structural effects of the N solvents (wherein $\delta_c$ is a real number from 0.0 to 1.0, and $\Delta del(S_i,S_j) = \Delta del(S_j,S_i)$).

In addition, the present invention provides a system for evaluating the similarity of structural effects of solvents determining solvent reactivity, comprising:

a selection module configured to select N solvents used for measuring the structural effects of solvents (wherein N is a natural number of 3 or more); and an evaluation module configured to evaluate the structural effects of the N solvents selected using the selection module and to include the following first to fourth data input modules:

a first data input module for calculating $R(S_i)$ for the solvent $S_i$ among the N solvents selected using the selection module, using Equation 1 to 3 below;

$$R(S_i) = \frac{k_1 \times MV_1(S_i)^2 + k_2 \times MV_2(S_i) \times MV_{base}(S_i)}{MV_{base}(S_i) \times MV_1(S_i)} \quad \text{[Equation 1]}$$

$$MV_1(S_i) = m(S_i) \times N_A \quad \text{[Equation 2]}$$

$$MV_2(S_i) = w_1 \times \pi \times Rd^3 \quad \text{[Equation 3]}$$

(in Equations 1 to 3, $S_i$ is the $i^{th}$ solvent among the selected N solvents, $MV_{base}(S_i)$ represents the molar volume for the solvent $S_i$, $m(S_i)$ represents the molecular volume for the solvent $S_i$ and is a McGowan Molecular volume or a van der Waals volume, $N_A$ is the Avogadro constant, Rd represents a characteristic length for a molecular structure and is a Molecular Radius of Gyration, the constants $k_1$ and $k_2$ are real numbers excluding 0.0, and the constant $w_1$ is a real number greater than 0.0);

a second data input module for setting a normal distribution using an average (AVG) and a standard deviation (SD) of N $R(S_i)$ values calculated using the first data input module, thus calculating a cumulative distribution function for the N $R(S_i)$ values to determine a cumulative probability value $\rho(S_i)$;

a third data input module for calculating $\Delta del(S_i,S_j)$, as a cumulative probability value difference for the solvents $S_i$ and $S_j$, using Equation 4 below:

$$\Delta del(S_i,S_j) = |\rho(S_i) - \rho(S_j)| \quad \text{[Equation 4]}$$

(in Equation 4, $S_i$ is the $i^{th}$ solvent among the selected N solvents, and $S_j$ is the $j^{th}$ solvent among the selected N solvents); and a fourth data input module for comparing $\Delta del(S_i,S_j)$ for the solvents $S_i$ and $S_j$ calculated using the third data input module with the set cut-off value, whereby when $\Delta del(S_i,S_j)$ is equal to or less than the cut-off value $\delta_c$, structural effects of the solvents $S_i$ and $S_j$ are determined to be similar, and when $\Delta del(S_i,S_j)$ is greater than the cut-off value $\delta_c$, structural effects of the solvents $S_i$ and $S_j$ are determined to be different, thus quantitatively evaluating the structural effects of the N solvents (wherein $\delta_c$ is a real number from 0.0 to 1.0, and $\Delta del(S_i,S_j) = \Delta del(S_j,S_i)$).

Advantageous Effects

According to the present invention, a method of evaluating the similarity of structural effects of solvents determining solvent reactivity is capable of quantitatively measuring the characteristics of solvents having similar structural effects. Therefore, according to the present invention, the method of quantitatively evaluating the structural effects of the solvents is expected to be considerably useful in terms of developing a novel method for improving the reactivity of a solvent or designing a reaction having novel characteristics.

BEST MODE

Hereinafter, a detailed description will be given of the present invention.

For reference, constants defined in the following Equations of the present invention are values that are determined within a range in which the method of the present invention works well.

In the present invention, the term "structural effect" refers to, upon reaction of two or more solvent functional groups, a difference in reactivity due to the constituent atoms around the functional groups.

For example, $H_2O$ is assumed to be produced through the reaction between a methyl functional group ($-CH_3$) of an "A" material and a hydroxyl group ($-OH$) of a "B" material. As such, when the methyl group ($-CH_3$) is located at the outside of the molecule, it may efficiently react with the hydroxyl group ($-OH$). However, when the methyl group ($-CH_3$) is surrounded by the other molecules of the A material, it may not come into contact with the hydroxyl group ($-OH$), in which case the reaction does not occur. This difference is referred to as a reactivity difference due to the structural effect.

In the present invention, the solvent may be a solid or liquid.

The present invention addresses a method of evaluating the similarity of structural effects of solvents determining solvent reactivity, comprising the steps of:

a) selecting N solvents used for measuring the structural effects of solvents (wherein N is a natural number of 3 or more); and b) evaluating the structural effects of the N solvents selected in step a) through the following steps of i) to iv):

i) calculating $R(S_i)$ for the solvent $S_i$, among the N solvents selected in step a), using Equations 1 to 3 below;

$$R(S_i) = \frac{k_1 \times MV_1(S_i)^2 + k_2 \times MV_2(S_i) \times MV_{base}(S_i)}{MV_{base}(S_i) \times MV_1(S_i)} \quad \text{[Equation 1]}$$

$$MV_1(S_i) = m(S_i) \times N_A \quad \text{[Equation 2]}$$

$$MV_2(S_i) = w_1 \times \pi \times Rd^3 \quad \text{[Equation 3]}$$

(in Equations 1 to 3, $S_i$ is the $i^{th}$ solvent among the selected N solvents, $MV_{base}(S_i)$ represents the molar volume for the solvent $S_i$, $m(S_i)$ represents the molecular volume for the solvent $S_i$ and is a McGowan Molecular volume or a van der Waals volume, $N_A$ is the Avogadro constant, Rd represents a characteristic length for a molecular structure and is a Molecular Radius of Gyration, the constants $k_1$ and $k_2$ are real numbers excluding 0.0, and the constant $w_1$ is a real number greater than 0.0);

ii) setting a normal distribution using an average (AVG) and a standard deviation (SD) of N $R(S_i)$ values calculated in step i), thus calculating a cumulative distribution function for the N $R(S_i)$ values to determine a cumulative probability value $\rho(S_i)$;

iii) calculating $\Delta del(S_i,S_j)$, as a cumulative probability value difference for solvents $S_i$ and $S_j$, using Equation 4 below:

$$\Delta del(S_i,S_j) = |\rho(S_i) - \rho(S_j)| \quad \text{[Equation 4]}$$

(in Equation 4, $S_i$ is the $i^{th}$ solvent among the selected N solvents, and $S_j$ is the $j^{th}$ solvent among the selected N solvents); and iv) comparing $\Delta del(S_i,S_j)$ for the solvents $S_i$ and $S_j$ calculated in step iii) with the set cut-off value, whereby when $\Delta del(S_i,S_j)$ is equal to or less than the cut-off value $\delta_c$, the structural effects of the solvents $S_i$ and $S_j$ are determined to be similar, and when $\Delta del(S_i,S_j)$ is greater than the cut-off value $\delta_c$, the structural effects of the solvents $S_i$ and $S_j$ are determined to be different, thus quantitatively evaluating the structural effects of the N solvents (wherein $\delta_c$ is a real number from 0.0 to 1.0, and $\Delta del(S_i,S_j) = \Delta del(S_j,S_i)$).

Specifically, step a) is selecting N solvents used for measuring the structural effects of solvents, wherein N is preferably a natural number of at least 3, and when N is greater than 3, N is not particularly limited, but is preferably a natural number from 3 to 100. The present invention aims at classifying solvents having similar structural effects. As the number N of solvents to be classified increases, the solvents may exhibit an overlapping effect. For example, at N=3, when the solvents are A1, A2, and A3, A1 and A2 may be found to be similar and A3 to be dissimilar thereto through the application of the present invention. If N is $N_1$, which is a natural number of 100 or more, A2 may become similar to A1 or to A10 in the range from A1 to $AN_1$. When similar phenomena overlap in this way, N is limited to the range of 3 to 100 taking into consideration the difficulty in distinguishing them even through the present invention.

In the evaluation of the structural effects of the solvents, the similarity of the reactivities of the solvents is evaluated, thus classifying the solvents.

The measurement of the structural effects of the N solvents selected in step a) may be performed through the calculation in step b), as described below.

Step b) is evaluating the structural effects of the N solvents selected in step a) and includes the steps of i) to iv). More preferably, in Equation 1 of step b), the constant $k_1$ is a real number from 0.0 to 4.0 and the constant $k_2$ is a real number from 0.0 to 10.0, and in Equation 3 of step b), the constant $w_1$ is a real number from 0.0 to 3.0.

In step b), the cut-off value $\delta_c$ is not particularly limited, but is preferably a real number from 0.0 to 1.0, and more preferably a real number from 0.01 to 0.40. The cut-off value, which is a reference value, is a flexible value that may vary depending on the kinds of solvents to be evaluated. In this case, when the magnitude of $\Delta\mathrm{del}(S_i,S_j)$ is equal to or less than the preset cut-off value, the structural effects of the solvents $S_i$ and $S_j$ are determined to be similar, and otherwise, the structural effects of the solvents may be determined to be different. Through the above quantitative evaluation, solvents having similar structural effects may be identified.

$\Delta\mathrm{del}(S_i,S_j)<\delta_c \rightarrow$ similar structural effects
$\Delta\mathrm{del}(S_i,S_j)>\delta_c \rightarrow$ different structural effects
$\Delta\mathrm{del}(S_i,S_j)=\Delta\mathrm{del}(S_j,S_i)$ In addition, the present invention addresses a system for evaluating the similarity of structural effects of solvents determining solvent reactivity using the aforementioned evaluation method.

According to the present invention, the system for evaluating the similarity of structural effects of solvents determining solvent reactivity comprises:

a selection module configured to select N solvents used for measuring the structural effects of solvents (wherein N is a natural number of 3 or more); and an evaluation module configured to evaluate the structural effects of the N solvents selected using the selection module and to include the following first to fourth data input modules:

a first data input module for calculating $R(S_i)$ for the solvent $S_i$ among the N solvents selected using the selection module, using Equation 1 to 3 below;

$$R(S_i) = \frac{k_1 \times MV_1(S_i)^2 + k_2 \times MV_2(S_i) \times MV_{base}(S_i)}{MV_{base}(S_i) \times MV_1(S_i)} \quad [\text{Equation 1}]$$

$$MV_1(S_i) = m(S_i) \times N_A \quad [\text{Equation 2}]$$

$$MV_2(S_i) = w_1 \times \pi \times Rd^3 \quad [\text{Equation 3}]$$

(in Equations 1 to 3, $S_i$ is the $i^{th}$ solvent among the selected N solvents, $MV_{base}(S_i)$ represents the molar volume for the solvent $S_i$, $m(S_i)$ represents the molecular volume for the solvent $S_i$ and is a McGowan Molecular volume or a van der Waals volume, $N_A$ is the Avogadro constant, Rd represents a characteristic length for a molecular structure and is a Molecular Radius of Gyration, the constants $k_1$ and $k_2$ are real numbers excluding 0.0, and the constant $w_1$ is a real number greater than 0.0);

a second data input module for setting a normal distribution using an average (AVG) and a standard deviation (SD) of N $R(S_i)$ values calculated using the first data input module, thus calculating a cumulative distribution function for the N $R(S_i)$ values to determine a cumulative probability value $\rho(S_i)$;

a third data input module for calculating $\Delta\mathrm{del}(S_i,S_j)$, as a cumulative probability value difference for the solvents $S_i$ and $S_j$, using Equation 4 below:

$$\Delta\mathrm{del}(S_i,S_j)=|\rho(S_i)-\rho(S_j)| \quad [\text{Equation 4}]$$

(in Equation 4, $S_i$ is the $i^{th}$ solvent among the selected N solvents, and $S_j$ is the $j^{th}$ solvent among the selected N solvents); and a fourth data input module for comparing $\Delta\mathrm{del}(S_i,S_j)$ for the solvents $S_i$ and $S_j$ calculated using the third data input module with the set cut-off value, whereby when $\Delta\mathrm{del}(S_i,S_j)$ is equal to or less than the cut-off value $\delta_c$, the structural effects of the solvents $S_i$ and $S_j$ are determined to be similar, and when $\Delta\mathrm{del}(S_i,S_j)$ is greater than the cut-off value $\delta_c$, the structural effects of the solvents $S_i$ and $S_j$ are determined to be different, thus quantitatively evaluating the structural effects of the N solvents (wherein $\delta_c$ is a real number from 0.0 to 1.0, and $\Delta\mathrm{del}(S_i,S_j)=\Delta\mathrm{del}(S_j,S_i)$).

Specifically, the selection module is configured to select N solvents used for measuring the structural effects of solvents, and N is preferably a natural number of at least 3. When N is greater than 3, N is not particularly limited, but is preferably a natural number from 3 to 100.

In the evaluation of the structural effects of the solvents, the similarity of the reactivities of the solvents is evaluated, thus classifying the solvents.

The measurement of the structural effects of the N solvents selected using the selection module may be performed through the calculation using the evaluation module, as described below.

The evaluation module is configured to evaluate the structural effects of the N solvents selected using the selection module and to include the first to fourth data input modules. More preferably, in Equation 1 of the evaluation module, the constant $k_1$ is a real number from 0.0 to 4.0 and the constant $k_2$ is a real number from 0.0 to 10.0, and in Equation 3 of the evaluation module, the constant $w_1$ is a real number from 0.0 to 3.0.

The cut-off value $\delta_c$ of the evaluation module is preferably a real number from 0.0 to 1.0, and more preferably a real number from 0.01 to 0.40. The cut-off value, which is a reference value, is a flexible value that may vary depending on the kinds of solvents to be evaluated. In this case, when the magnitude of $\Delta\mathrm{del}(S_i,S_j)$ is equal to or less than the preset cut-off value, the structural effects of the solvents $S_i$ and $S_j$ are determined to be similar, and otherwise, the structural effects of the solvents may be determined to be different. Through the above quantitative evaluation, solvents having similar structural effects may be identified.

$\Delta\mathrm{del}(S_i,S_j)<\delta_c \rightarrow$ similar structural effects
$\Delta\mathrm{del}(S_i,S_j)>\delta_c \rightarrow$ different structural effects
$\Delta\mathrm{del}(S_i,S_j)=\Delta\mathrm{del}(S_j,S_i)$ As used herein, the term "module" refers to a unit that is responsible for a specific function or operation, and may be embodied by hardware and software, either alone or in combination.

Mode for Invention

A better understanding of the present invention may be obtained via the following examples, which are set forth to illustrate, but are not to be construed as limiting the scope of the present invention. The scope of the present invention is given by the claims, and also contains all modifications within the meaning and range equivalent to the claims.

EXAMPLE

Step 1. Selection of N Solvents the Structural Effects of Which are to be Measured As solvents for evaluating structural similarity, the following eight solvents were selected.

1. Ethanol 2. Isopropyl alcohol 3. Acetic acid 4. n-Butanol 5. Formic acid 6. n-Pentanol 7. Benzyl alcohol 8. n-Hexanol Step 2. Evaluation of Structural Effects of Selected N Solvents $R(S_i)$ values for the eight solvents $S_i$ selected in step 1 were calculated using Equations 1 to 3 below. The $R(S_i)$ values for the respective solvents are shown in Table 1 below.

$$R(S_i) = \frac{k_1 \times MV_1(S_i)^2 + k_2 \times MV_2(S_i) \times MV_{base}(S_i)}{MV_{base}(S_i) \times MV_1(S_i)}$$ [Equation 1]

$$MV_1(S_i) = m(S_i) \times N_A$$ [Equation 2]

$$MV_2(S_i) = w_1 \times \pi \times Rd^3$$ [Equation 3]

In the above calculation, $m(S_i)$ was set to a McGowan Molecular volume for each solvent $S_i$, and Rd was set to a Molecular Radius of Gyration for each solvent $S_i$. The constants $k_1$ and $k_2$ were set to 1.0 and 0.12, respectively, and the constant $w_1$ was set to 1.3. The Avogadro constant $N_A$ was set to about $6.02214 \times 10^{23}$ mol$^{-1}$. Here, the values for respective solvents were as follows: $m(S_1)$ was 27.1 ml/mol, $m(S_2)$ was 35.5 ml/mol, $m(S_3)$ was 28.0 ml/mol, $m(S_4)$ was 44.0 ml/mol, $m(S_5)$ was 19.5 ml/mol, $m(S_6)$ was 52.5 ml/mol, $m(S_7)$ was 55.1 ml/mol, and $m(S_8)$ was 61.0 ml/mol. Also, Rd1 was 1.20 Å, Rd2 was 1.38 Å, Rd3 was 1.27 Å, Rd4 was 1.92 Å, Rd5 was 1.03 Å, Rd6 was 2.28 Å, Rd7 was 2.00 Å, and Rd8 was 2.64 Å.

TABLE 1

| $S_i$ | Ethanol | Isopropyl alcohol | Acetic acid | n-Butanol | Formic acid | n-Pentanol | Benzyl alcohol | n-Hexanol |
|---|---|---|---|---|---|---|---|---|
| $R(S_i)$ | 0.481 | 0.484 | 0.508 | 0.527 | 0.531 | 0.552 | 0.575 | 0.578 |

Using the average (AVG) and the standard deviation (SD) of the $R(S_i)$ values of the eight solvents $S_i$, the normal distribution was set to thus calculate the cumulative distribution function, thereby determining, as a cumulative distribution function value, a cumulative probability value $\rho(S_i)$. The results are shown in Table 2 below.

TABLE 2

| $S_i$ | Ethanol | Isopropyl alcohol | Acetic acid | n-Butanol | Formic acid | n-Pentanol | Benzyl alcohol | n-Hexanol |
|---|---|---|---|---|---|---|---|---|
| $\rho(S_i)$ | 0.098 | 0.113 | 0.281 | 0.469 | 0.515 | 0.717 | 0.882 | 0.898 |

Thereafter, a difference in cumulative probability values $\rho(S_i)$ as the cumulative distribution function values for $S_i$ representing the i$^{th}$ solvent and $S_j$ representing the j$^{th}$ solvent among the eight solvents was calculated using Equation 4 below.

$$\Delta del(S_i, S_j) = |\rho(S_i) - \rho(S_j)|$$ [Equation 4]

In the case where a total of eight solvents were selected, when $\Delta del(S_i, S_j)$, calculated using Equation 4, was equal to or less than the set cut-off value $\delta_c$, solvents having similar structural effects were searched for and evaluated. As results thereof, the solvents, the structural effects of which are deemed to be similar, are shown in Table 3 below. Here, the cut-off value $\delta_c$ was set to 0.05.

$\Delta del(S_i, S_j) \leq \delta_c \rightarrow$similar structural effects

TABLE 3

| $S_i$ | $S_j$ | $\Delta del(S_i, S_j)$ |
|---|---|---|
| Ethanol | Isopropyl alcohol | 0.015 |
| n-Butanol | Formic acid | 0.046 |
| Benzyl alcohol | n-Hexanol | 0.016 |

Based on the results of quantitative evaluation through the above procedures, when the cut-off value $\delta_c$ was 0.05, the solvents determined to exhibit similar structural effects, meeting the cut-off value or less, were the following three cases.

(1) Ethanol and isopropyl alcohol (2) n-Butanol and formic acid (3) Benzyl alcohol and n-hexanol Furthermore, among the above solvents, no solvents were determined to exhibit structural effects similar to those of acetic acid and n-pentanol, as was confirmed through the calculation results.

Through the above method, similar structural effects of the solvents can be quantitatively measured, thus enabling the development of a novel method for improving solvent reactivity or designing a reaction having novel characteristics.

The invention claimed is:

1. A method of evaluating similarities in the structural effects of solvents in order to determine solvent reactivity, comprising the steps of:

a) selecting N solvents used for the measuring of structural effects of said N solvents, wherein N is a natural number of 3 or more;
b) evaluating the structural effects of the N solvents selected in step a) through the following steps i) to iv):
i) calculating $R(S_i)$ for a solvent $S_i$ among the N solvents selected in step a), using Equations 1 to 3 below;

$$R(S_i) = \frac{k_1 \times MV_1(S_i)^2 + k_2 \times MV_2(S_i) \times MV_{base}(S_i)}{MV_{base}(S_i) \times MV_1(S_i)} \quad \text{[Equation 1]}$$

$$MV_1(S_i) = m(S_i) \times N_A \quad \text{[Equation 2]}$$

$$MV_2(S_i) = w_1 \times \pi \times Rd^3 \quad \text{[Equation 3]}$$

wherein $S_i$ is an $i^{th}$ solvent among the selected N solvents, $MV_{base}(S_i)$ represents a molar volume for the solvent $S_i$, $m(S_i)$ represents a molecular volume for the solvent $S_i$ and is a McGowan Molecular volume or a van der Waals volume, $N_A$ is an Avogadro constant, Rd represents a characteristic length for a molecular structure and is a Molecular Radius of Gyration, constants $k_1$ and $k_2$ are real numbers excluding 0.0, and a constant $w_1$ is a real number greater than 0.0;
ii) calculating a cumulative distribution function for the N $R(S_i)$ values to determine a cumulative probability value $r(S_i)$ by setting a normal distribution using an average (AVG) and a standard deviation (SD) of N $R(S_i)$ values calculated in step i);
iii) calculating $\Delta\text{del}(S_i, S_j)$, as a cumulative probability value difference for solvents $S_i$ and $S_j$, using Equation 4 below:

$$\Delta\text{del}(S_i, S_j) = |\rho(S_i) - \rho(S_j)| \quad \text{[Equation 4]}$$

whereas $S_i$ is an $i^{th}$ solvent among the selected N solvents, and $S_j$ is a $j^{th}$ solvent among the selected N solvents; and
iv) quantitatively evaluating the structural effects of the N solvents by comparing $\Delta\text{del}(S_i, S_j)$ for the solvents $S_i$ and $S_j$ calculated in step iii) with a set cut-off value, whereby when $\Delta\text{del}(S_i, S_j)$ is equal to or less than the cut-off value $\delta_c$, structural effects of the solvents $S_i$ and $S_j$ are determined to be similar, and when $\Delta\text{del}(S_i, S_j)$ is greater than the cut-off value $\delta_c$, structural effects of the solvents $S_i$ and $S_j$ are determined to be different, wherein $\delta_c$ is a real number from 0.0 to 1.0, and $\Delta\text{del}(S_i, S_j) = \Delta\text{del}(S_j, S_i)$; and
c) classifying the solvents having similar structural effects evaluated in step b) and interchangeably using the solvents in the reaction with a specific material.

2. The method of claim 1, wherein in step a), N is a natural number from 3 to 100.

3. The method of claim 1, wherein in step b), the constant $k_1$ is a real number greater than 0.0 to 4.0 and the constant $k_2$ is a real number greater than 0.0 to 10.0.

4. The method of claim 1, wherein the constant $w_1$ in step b) is a real number greater than 0.0 to 3.0.

5. The method of claim 1, wherein the cut-off value $\delta_c$ in step b) is a real number from 0.01 to 0.40.

6. A system for evaluating similarities in the structural effects of solvents in order to determine solvent reactivity, comprising:
a selection module configured to select N solvents used for the measuring of structural effects of said N solvents, wherein N is a natural number of 3 or more, and
an evaluation module for evaluating structural effects of the N solvents selected using the selection module and to include the following first to fourth data input modules:
a first data input module for calculating $R(S_i)$ for a solvent $S_i$ among the N solvents selected using the selection module, using Equation 1 to 3 below;

$$R(S_i) = \frac{k_1 \times MV_1(S_i)^2 + k_2 \times MV_2(S_i) \times MV_{base}(S_i)}{MV_{base}(S_i) \times MV_1(S_i)} \quad \text{[Equation 1]}$$

$$MV_1(S_i) = m(S_i) \times N_A \quad \text{[Equation 2]}$$

$$MV_2(S_i) = w_1 \times \pi \times Rd^3 \quad \text{[Equation 3]}$$

wherein $S_i$ is an $i^{th}$ solvent among the selected N solvents, $MV_{base}(S_i)$ represents a molar volume for the solvent $S_i$, $m(S_i)$ represents a molecular volume for the solvent $S_i$ and is a McGowan Molecular volume or a van der Waals volume, $N_A$ is an Avogadro constant, Rd represents a characteristic length for a molecular structure and is a Molecular Radius of Gyration, constants $k_1$ and $k_2$ are real numbers excluding 0.0, and a constant $w_1$ is a real number greater than 0.0;
a second data input module for calculating a cumulative distribution function for the N $R(S_i)$ values to determine a cumulative probability value $\rho(S_i)$ by setting a normal distribution using an average (AVG) and a standard deviation (SD) of N $R(S_i)$ values calculated using the first data input module;
a third data input module for calculating $\Delta\text{del}(S_i, S_j)$, as a cumulative probability value difference for the solvents $S_i$ and $S_j$, using Equation 4 below:

$$\Delta\text{del}(S_i, S_j) = |\rho(S_i) - \rho(S_j)| \quad \text{[Equation 4]}$$

wherein $S_i$ is an $i^{th}$ solvent among the selected N solvents, and $S_j$ is a $j^{th}$ solvent among the selected N solvents;
a fourth data input module for quantitatively evaluating the structural effects of the N solvents comparing $\Delta\text{del}(S_i, S_j)$ for the solvents $S_i$ and $S_j$ calculated using the third data input module with a set cut-off value, whereby when $\Delta\text{del}(S_i, S_j)$ is equal to or less than the cut-off value $\rho_c$, structural effects of the solvents $S_i$ and $S_j$ are determined to be similar, and when $\Delta\text{del}(S_i, S_j)$ is greater than the cut-off value $\rho_c$, structural effects of the solvents $S_i$ and $S_j$ are determined to be different, wherein $\rho_c$ is a real number from 0.0 to 1.0, and $\Delta\text{del}(S_i, S_j) = \Delta\text{del}(S_j, S_i)$ and
wherein the evaluating of the structural effects of the solvents comprises classifying the solvents by evaluating similarity of reactivity of the solvents.

7. The system of claim 6, wherein N of the selection module is a natural number from 3 to 100.

8. The system of claim 6, wherein of the evaluation module, the constant $k_1$ is a real number greater than 0.0 to 4.0 and the constant $k_2$ is a real number greater than 0.0 to 10.0.

9. The system of claim 6, wherein the constant $w_1$ of the evaluation module is a real number greater than 0.0 to 3.0.

10. The system of claim 6, wherein the cut-off value $\delta_c$ of the evaluation module is a real number from 0.01 to 0.40.

* * * * *